United States Patent
Akiyoshi

(10) Patent No.: US 9,810,677 B2
(45) Date of Patent: Nov. 7, 2017

(54) UREA WATER SUITABILITY DETERMINATION DEVICE

(71) Applicant: Hino Motors, Ltd., Tokyo (JP)

(72) Inventor: Toshiya Akiyoshi, Hino (JP)

(73) Assignee: HINO MOTORS, LTD., Tokyo (JP)

( * ) Notice: Subject to any disclaimer, the term of this patent is extended or adjusted under 35 U.S.C. 154(b) by 76 days.

(21) Appl. No.: 14/786,061

(22) PCT Filed: Jun. 12, 2014

(86) PCT No.: PCT/JP2014/065603
§ 371 (c)(1),
(2) Date: Oct. 21, 2015

(87) PCT Pub. No.: WO2014/203802
PCT Pub. Date: Dec. 24, 2014

(65) Prior Publication Data
US 2016/0146776 A1 May 26, 2016

(30) Foreign Application Priority Data
Jun. 17, 2013 (JP) ................. 2013-126775

(51) Int. Cl.
*G01N 33/18* (2006.01)
*F01N 11/00* (2006.01)
(Continued)

(52) U.S. Cl.
CPC ....... *G01N 33/1826* (2013.01); *F01N 3/2066* (2013.01); *F01N 11/002* (2013.01);
(Continued)

(58) Field of Classification Search
CPC .. G01N 33/1826; G01N 25/00; G01N 29/024; F01N 3/2066; F01N 11/002
See application file for complete search history.

(56) References Cited

U.S. PATENT DOCUMENTS 7,467,512 B2 * 12/2008 Nishina ................. F01N 3/208
60/274
2007/0163240 A1 7/2007 Nishina et al.
(Continued)

FOREIGN PATENT DOCUMENTS

EP  1681444 A1  7/2006
EP  1900915 A   3/2008
(Continued)

OTHER PUBLICATIONS

English Machine Translation of Kazutaka, JP 2007-192045 A, Aug. 2, 2007, Translated Mar. 2017.*
(Continued)

*Primary Examiner* — Hezron E Williams
*Assistant Examiner* — David Z Huang
(74) *Attorney, Agent, or Firm* — Kilpatrick Townsend & Stockton LLP

(57) ABSTRACT

A concentration detecting section detects a concentration of urea water and outputs the detected value. A determining section determines whether the urea water is suitable by using the detected value. A temperature detecting section detects temperatures of detection targets. The detection targets have temperatures that are different from one another during operation of an engine. The determining section is adapted to calculate a temperature difference between temperatures of a particular detection target and another detection target and start determining whether the urea water is suitable when a determination start condition including that the temperature difference is within a reference range is satisfied. The reference range is defined as a range of temperature differences in which it is determined that the urea water is in a quiescent state, which is suitable for the determination.

5 Claims, 4 Drawing Sheets

(51) Int. Cl.
*G01N 25/00* (2006.01)
*G01N 29/024* (2006.01)
*F01N 3/20* (2006.01)

(52) U.S. Cl.
CPC .......... *G01N 25/00* (2013.01); *G01N 29/024* (2013.01); *F01N 2550/05* (2013.01); *F01N 2610/02* (2013.01); *F01N 2900/08* (2013.01); *F01N 2900/1811* (2013.01); *F01N 2900/1818* (2013.01); *G01N 2291/011* (2013.01); *Y02T 10/24* (2013.01); *Y02T 10/47* (2013.01)

(56) References Cited

U.S. PATENT DOCUMENTS

2012/0118059 A1* 5/2012 Reimer ................ F01N 3/2066
  73/290 V
2014/0157879 A1   6/2014 Zamani et al.

FOREIGN PATENT DOCUMENTS

| JP | 2002371831 A | 12/2002 |
|----|--------------|---------|
| JP | 20030286888 A | 10/2003 |
| JP | 2004044432 A | 2/2004 |
| JP | 2005133541 A | 5/2005 |
| JP | 2007192045 A | 8/2007 |
| JP | 2009062032 A | 3/2009 |
| JP | 2012002060 S | 1/2012 |
| WO | 2011078692 A1 | 6/2011 |
| WO | WO 2013/009240 A1 | 1/2013 |

OTHER PUBLICATIONS

Extended European Search Report dated Nov. 14, 2016 corresponding to the European patent application No. 14813624.5, seven pages.
Translation of the International Preliminary Report on Patentability dated Dec. 22, 2015 corresponding to PCT/JP2014/065603, six pages.
International Search Report dated Aug. 12, 2014 corresponding to PCT/JP2014/065603, two pages.
Translation of Office Action corresponding to Japanese Application No. 2013-126775, dated Jun. 2, 2017, 4 pages.

* cited by examiner

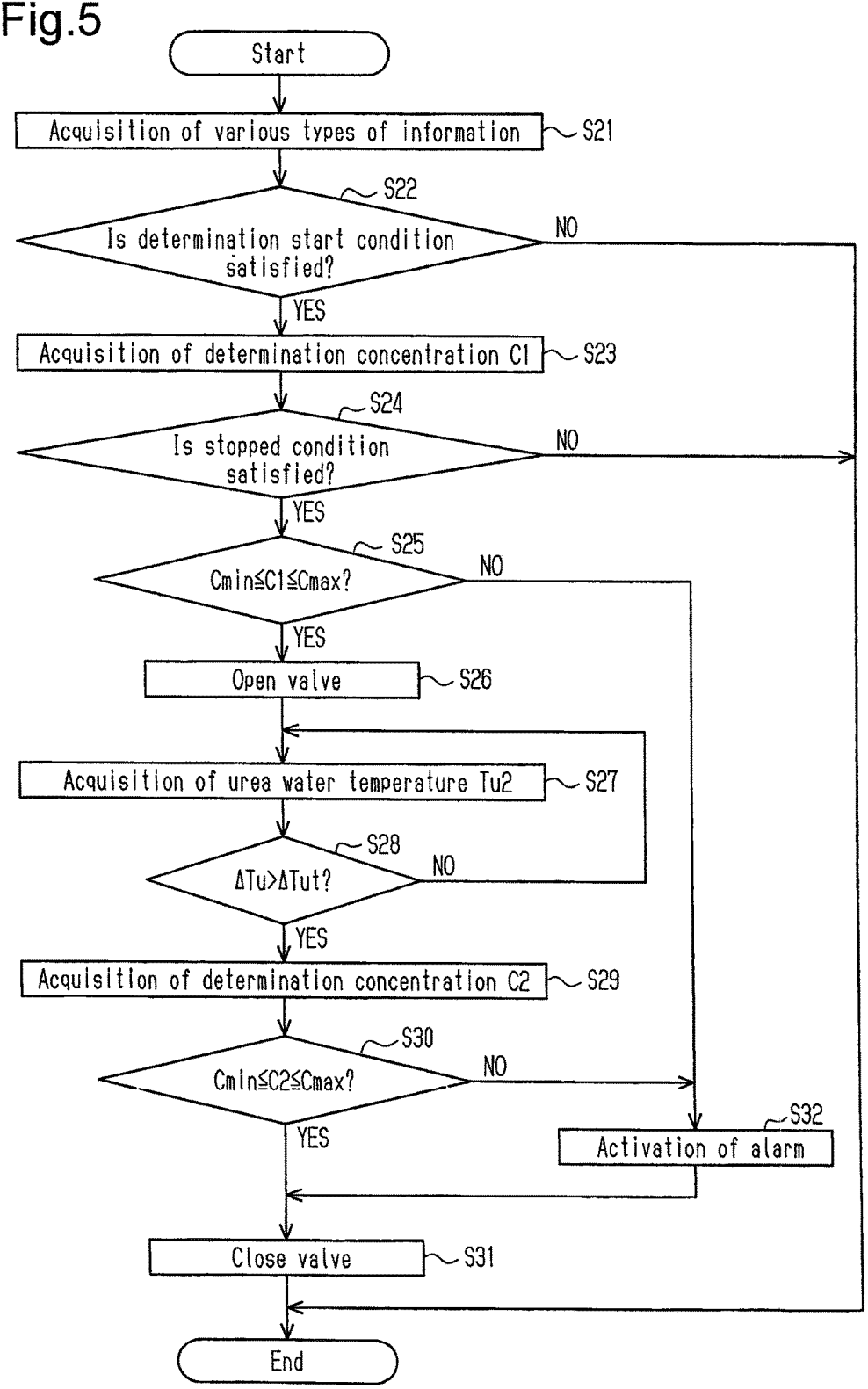

UREA WATER SUITABILITY DETERMINATION DEVICE

TECHNICAL FIELD

The techniques of the present disclosure relate to a urea water suitability determination device that determines suitability of urea water.

BACKGROUND ART

A conventional exhaust gas purifier is known to purify nitrogen oxide (hereinafter, refer to as NOx) in exhaust gas. The exhaust gas purifier includes a urea water supply system, which supplies urea water to the exhaust gas, and a selective reduction catalyst, into which the exhaust gas supplied with the urea water flows. For example, when water in the urea water is excessively evaporated, or when a tank is filled with fluid that does not meet standards, an abnormality occurs in the quality of the urea water. Variation in the quality of the urea water changes the amount of urea water necessary for obtaining desired purification performance in the exhaust gas purifier. On this account, the technique disclosed in Patent Document 1 causes a sensor to detect the concentration of the urea water in the tank, and suitability of the urea water is determined based on the detected value. The driver is warned when an abnormality occurs in the quality of the urea water.

PRIOR ART DOCUMENT

Patent Document

Patent Document 1: Japanese Laid-Open Patent Publication No. 2002-371831

SUMMARY OF THE INVENTION

Problem that the Invention is to Solve

In recent years, it has been desired to further improve the reliability of a determination result in the suitability of urea water based on its concentration.

An object of the techniques of the present disclosure is to provide a urea water suitability determination device that improves the reliability of a determination result in the suitability of urea water.

Means for Solving the Problems

One aspect of the present disclosure is to provide a urea water suitability determination device. The urea water suitability determination device includes a concentration detecting section, a determining section, and a temperature detecting section. The concentration detecting section detects a concentration of urea water and outputs the detected value. The determining section determines whether the urea water is suitable by using the detected value output from the concentration detecting section. The temperature detecting section detects temperatures of a plurality of detection targets at different locations in a vehicle. The detection targets have temperatures that are different from one another during operation of an engine. The determining section is adapted to calculate a temperature difference between a temperature of a particular detection target and a temperature of another detection target among the detection targets and, when a determination start condition is satisfied, start determining whether the urea water is suitable. The determination start condition includes that the temperature difference is within a reference range. The reference range is defined as a range of temperature differences in which it is determined that the urea water is in a quiescent state, which is suitable for the determination.

BRIEF DESCRIPTION OF THE DRAWINGS

FIG. 5 is a flowchart showing determination processes of the suitability determination device of FIG. 3.

EMBODIMENTS OF THE INVENTION

First Embodiment

A urea water suitability determination device according to a first embodiment will now be described with reference to FIGS. 1 and 2.

Figure 1:
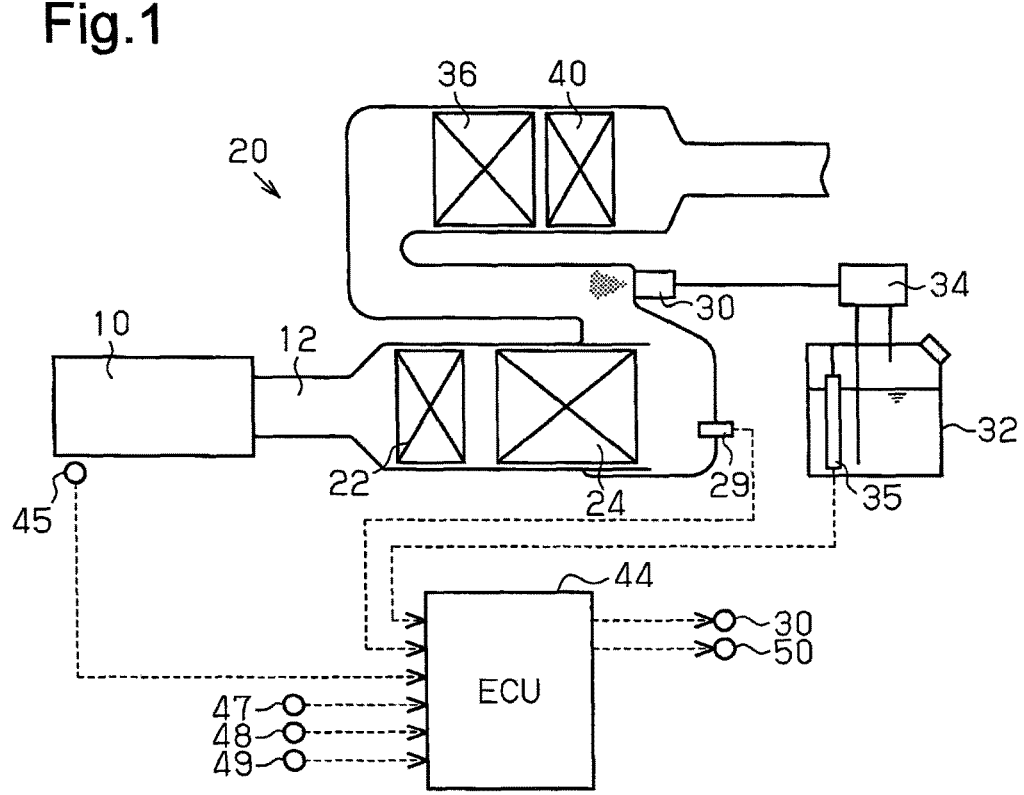
FIG. 1 is a schematic view of an exhaust gas purifier having a urea water suitability determination device according to a first embodiment.

As shown in FIG. 1, a diesel engine 10 (hereinafter, referred to simply as the engine 10) includes an exhaust gas purifier 20 for purifying exhaust gas, which is arranged in an exhaust passage 12. Exhaust gas that has flowed into the exhaust gas purifier 20 flows into a first stage oxidation catalyst 22.

The first stage oxidation catalyst 22 is a diesel oxidation catalyst (DOC), which oxidizes and transforms hydrocarbons (HC), carbon monoxide (CO), and nitric monoxide (NO) contained in the exhaust gas into water, carbon dioxide, nitrogen dioxide, and the like. The first stage oxidation catalyst 22 includes, for example, a support, which is formed of alumina, silica, zeolite, and metal, such as platinum and palladium, and metal oxide, which are supported by the support.

The exhaust gas that has passed through the first stage oxidation catalyst 22 flows into a diesel particulate filter (DPF) 24. The DPF 24 is formed of ceramics and a metal porous body to capture particulate matter (PM) in the exhaust gas. In a regeneration process of the DPF 24, the temperature of the exhaust gas flowing into the DPF 24 is raised. This is realized, for example, by supplying combustion gas from a burner (not shown) to a portion of the exhaust passage 12 that is located upstream of the first stage oxidation catalyst 22, or by supplying fuel from a fuel injection valve (not shown) to the portion.

An exhaust gas temperature sensor 29 is arranged downstream of the DPF 24 and upstream of a selective reduction catalyst 36, which will be described later. The exhaust gas temperature sensor 29 serves as a temperature detecting section for detecting a temperature of the exhaust passage 12 as a detection target. The exhaust gas temperature sensor 29 detects a temperature in a portion of the exhaust passage 12 that is located downstream of the DPF 24 at a predetermined control period. The exhaust gas temperature sensor 29 outputs, to the ECU 44, signal indicative of an exhaust gas temperature Tex, which is a detected value.

An electronically controlled injector 30 is arranged downstream of the exhaust gas temperature sensor 29 and supplies urea water, which is a reducing agent, to the exhaust passage 12. A pressure pump 34 pumps urea water stored in a tank 32 to the injector 30. A relief valve (not shown) is built in the pressure pump 34 so that the urea water in the tank 32 is pumped to the injector 30 at a predetermined pressure. The ECU 44 controls opening and closing of the injector 30. The urea water supplied to the exhaust gas is hydrolyzed to ammonia with heat of the exhaust gas.

A urea water quality sensor 35 (hereinafter, simply referred to as the "sensor 35") is arranged in the tank 32. The sensor 35 detects information of the urea water in the tank 32. The sensor 35 outputs, to the ECU 44, a signal indicative of a urea water temperature Tu, which is a temperature of the urea water, and a signal indicative of a liquid level indicative of the remaining amount of the urea water. The sensor 35 also measures a propagation velocity Vus of an ultrasonic wave in the urea water. The sensor 35 then calculates a urea water concentration C by correcting a value obtained from the measured propagation velocity Vus based on the urea water temperature Tu. The sensor 35 outputs a signal indicative of the urea water concentration C to the ECU 44. In other words, the sensor 35 functions as a concentration detecting section for detecting the urea water concentration C and functions as a temperature detecting section for detecting the urea water temperature Tu, which is a temperature of the urea water as a detection target. The injector 30, the tank 32, the pressure pump 34, the sensor 35, and the urea water form a urea water supply system.

A selective reduction catalyst 36 is arranged downstream of the injector 30. The selective reduction catalyst 36 performs selective catalytic reduction to reduce NOx using ammonia. The selective reduction catalyst 36 includes, for example, a support, which is formed of honeycomb ceramics, and high adsorptive zeolite or zirconia, which is supported by the support. NOx in the exhaust gas reacts with ammonia in catalysis of the selective reduction catalyst 36 and is reduced into nitrogen and water.

The exhaust gas that has passed through the selective reduction catalyst 36 flows into the second stage oxidation catalyst 40. The second stage oxidation catalyst 40 is an ammonia slip catalyst (ASC), which dissolves ammonia unconsumed in the reduction reaction of the selective reduction catalyst 36. The second stage oxidation catalyst 40 includes, for example, a support, which includes alumina, silica, and zeolite, metal, such as platinum and palladium, and metal oxide, which are supported by the support.

The ECU 44 is a microcomputer, which includes a CPU, a RAM, a ROM, and the like. As described above, the ECU 44 receives signals indicative of the urea water concentration C, the urea water temperature Tu, and the exhaust gas temperature Tex. In addition to those, the ECU 44 receives a signal indicative of a coolant temperature Tw from a coolant temperature sensor 45 at a predetermined control period. The coolant temperature sensor 45 serves as a temperature detecting section for detecting a temperature of coolant that cools the engine 10 as a detection target. During operation of the engine 10, the urea water temperature Tu, the exhaust gas temperature Tex, and the coolant temperature Tw are different from one another, and the detectable highest temperatures are also different. In other words, each of the detection targets for the temperature detecting section has a different temperature range during operation of the engine 10.

The ECU 44 receives signals from various types of sensors at a predetermined control period. The signals include a signal from a brake sensor 47, a signal from a gear position sensor 48, and a signal from a vehicle speed sensor 49. The signal from the brake sensor 47 is indicative of brake information Binf, which shows the operation state of the brake. The signal from the gear position sensor 48 is indicative of gear information Ginf, which shows the gear position. The signal from the vehicle speed sensor 49 is indicative of a vehicle speed V of the vehicle, which is equipped with the engine 10. The brake sensor 47, the gear position sensor 48, and the vehicle speed sensor 49 function as a parking information detecting section.

The ECU 44 executes various computations and processes based on information received from each of the sensors, and a control program and various types of data, which are stored in the ROM in advance. The ECU 44 executes a urea water supply process by controlling opening and closing of the injector 30. The ECU 44 as a suitability determination device executes a determination process that determines whether the urea water in the tank 32 is suitable, i.e., determines the suitability of the urea water. If the urea water is a regular product, which satisfies a desired quality, the urea water is determined as suitable. In the determination process, the ECU 44 functions as a determining section that determines the suitability of the urea water. When obtaining abnormality as a determination result, the ECU 44 activates an alarm 50 to notify the driver of the determination result.

Figure 2:
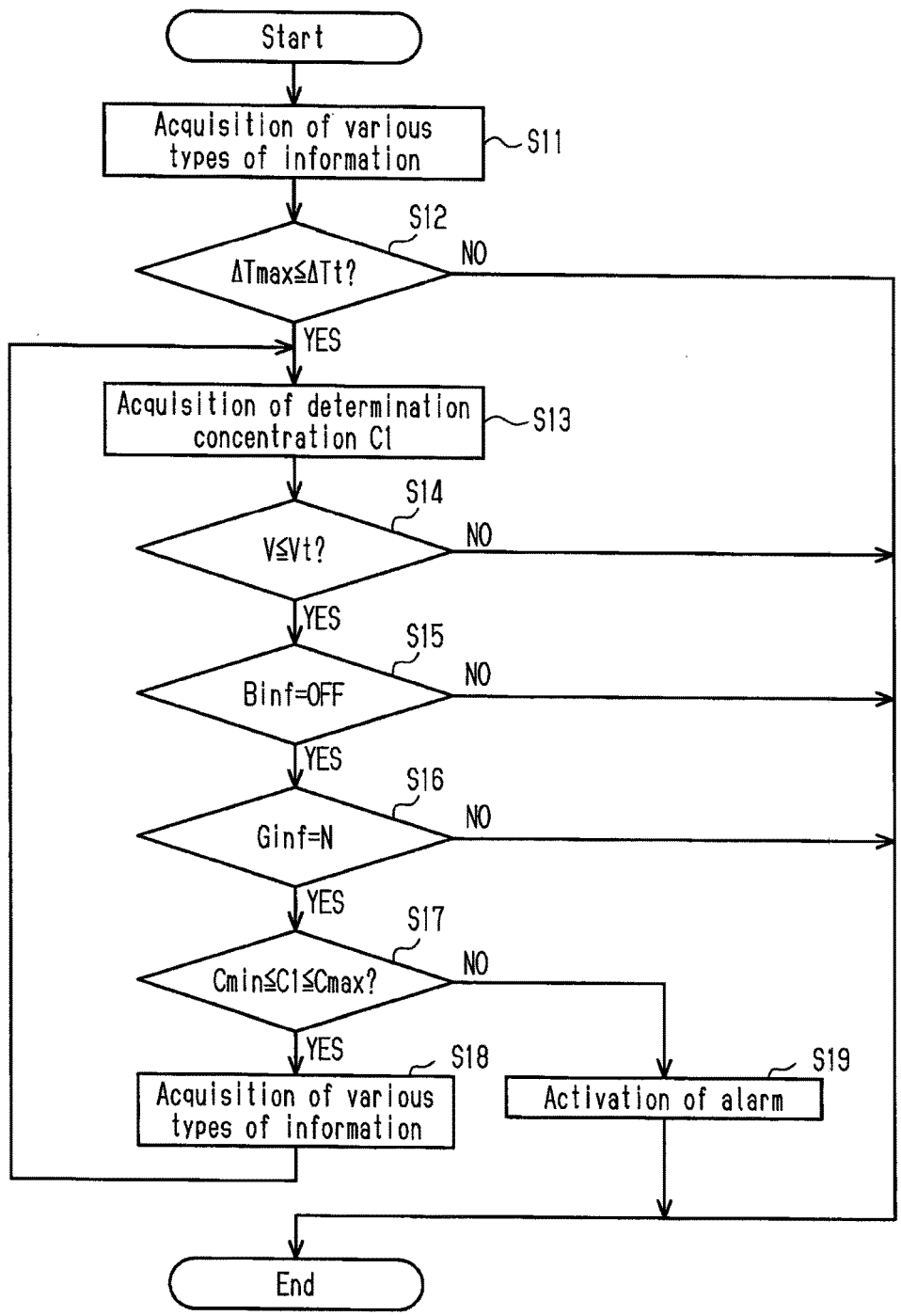
FIG. 2 is a flowchart showing a determination process in the suitability determination device of FIG. 1.

With reference to FIG. 2, the determination process according to the first embodiment will now be described. This determination process is executed every time the ignition of the vehicle is turned ON.

As shown in FIG. 2, the ECU 44 acquires various types of information at the initial step S11. Such information includes the exhaust gas temperature Tex, the urea water temperature Tu, the coolant temperature Tw, the brake information Binf, the gear information Ginf, and the vehicle speed V.

At the next step S12, the ECU 44 calculates a temperature difference between a particular detection target and another detection target among a plurality of detection targets. The ECU 44 then acquires a maximum value ΔTmax from the temperature differences. The ECU 44 determines whether the maximum value ΔTmax is within a reference range, which is less than or equal to a threshold ΔTt. The ECU 44 selects any two temperatures among the exhaust gas temperature Tex, the urea water temperature Tu, and the coolant temperature Tw as targets for the temperature difference calculation. The ECU 44 calculates the temperature difference between the selected two temperatures. The ECU 44 acquires the greatest value among the temperature differences as the maximum value ΔTmax. The ECU 44 determines whether the maximum value ΔTmax is within the reference range, which is less than or equal to the threshold ΔTt. The threshold ΔTt has the maximum value ΔTmax, e.g., 15° C. when the urea water is in a quiescent state, i.e., a state without vibrations, bubbles and the like after sufficient time has passed from the previous stop of the engine 10. The threshold ΔTt is a preset value in various types of data, which is determined through various types of experiments and simulations. For example, the temperature difference (Δ|Tex−Tw|) between the exhaust gas temperature Tex and the coolant temperature Tw and the temperature difference (Δ|Tw−Tu|) between the coolant temperature Tw and the urea water temperature Tu have different thresholds, with which it is determined that the urea water is in the quiescent state. In other words, any combinations of two targets are selected, and each of the combinations has a different threshold. With the threshold, it is determined that the urea water is in the quiescent state. The threshold $\Delta Tt$ has the greatest value among the thresholds of the temperature differences. Here, a determination start condition is defined as that the maximum value $\Delta Tmax$ is less than or equal to the threshold $\Delta Tt$.

When the maximum value $\Delta Tmax$ exceeds the threshold $\Delta Tt$ (step S12: NO), i.e., when the determination start condition is not satisfied, stopping time of the engine 10 is insufficient. Thus, ECU 44 determines that the urea water is not in the quiescent state and finishes a series of processes. In contrast, when the maximum value $\Delta Tmax$ is less than or equal to the threshold $\Delta Tt$ (step S12: YES), i.e., when the determination start condition is satisfied, the ECU 44 acquires a determination concentration C1 from the sensor 35 (step S13). The determination concentration C1 is a concentration for determining the suitability of the urea water. The ECU. 44 determines whether the vehicle speed V, which is acquired at step 11, is less than or equal to the threshold Vt, e.g. 0 km/h, (step S14).

When the vehicle speed V is less than or equal to the threshold Vt (step S14: YES), the ECU 44 determines whether the brake information Binf acquired at step 11 is OFF (step S15).

When the brake information Binf is OFF (step S15: YES), i.e., when the brake is not being operated, the ECU 44 determines whether the gear information Ginf acquired at step S11 is N, i.e., whether the gear position is neutral, i.e., whether the engine and the transmission are disconnected (step S16).

Here, a stopped condition is defined as a state in which the vehicle speed V is less than or equal to the threshold Vt (step S14); the brake information Binf is OFF (step S15); and the gear information Ginf is N (step S16). When the vehicle speed V is greater than the threshold Vt (step S14: NO); when the brake information Binf is not OFF (step S15: NO); or when the gear information Ginf is N (step S16: NO), the stopped condition is not satisfied. When the stopped condition is not satisfied, the ECU 44 determines that the vehicle is not in the stopped state and finishes the determination process.

When the gear information Ginf is N (step S16: YES), the ECU 44 determines whether the determination concentration C1 acquired at step S13 is within a normal range (step S17). The normal range is greater than or equal to a lower limit Cmin and less than or equal to an upper limit Cmax. When the determination concentration C1 is within the normal range, it is determined that the urea water is a regular product. The lower limit Cmin and the upper limit Cmax are provided in advance in the respective types of data and determined in consideration of measurement error of the sensor 35. The ECU 44 includes the determination start condition and the stopped condition as conditions to determine the suitability of the urea water.

When the determination concentration C1 deviates from the normal range (step S17: NO), the ECU 44 determines that the urea water in the tank 32 is abnormal and activates the alarm 50 (step S19). Thus, the ECU 44 warns the driver that the urea water in the tank 32 is abnormal, and finishes the series of processes.

In contrast, when the determination concentration C1 is within the normal range (step S17: YES), the ECU 44 determines that the urea water in the tank 32 is normal. The ECU 44 newly acquires the same type of information as the information acquired at step S11 (step S18) and moves to step S13. The ECU 44 repeats determination of suitability of the urea water until the stopped condition is no longer satisfied or until it is determined that the urea water is abnormal.

Operation of the determination process, which the ECU 44 executes in the first embodiment, will now be described.

In the determination process of the first embodiment, when the maximum value $\Delta Tmax$ is less than or equal to the threshold $\Delta Tt$, the urea water is in the quiescent state in comparison to a case in which the maximum value $\Delta Tmax$ exceeds the threshold $\Delta Tt$. Thus, the sensor 35 calculates the determination concentration C1 based on the propagation velocity Vus in the urea water, which is in the quiescent state. This decreases error of the determination concentration C1 relative to the actual concentration of the urea water. Thus, the reliability of the determination concentration C1 is increased, and eventually increases the reliability of the determination result in suitability of the urea water.

The urea water suitability determination device according to the first embodiment achieves the advantages listed below.

(1) The determination concentration C1 is calculated based on the propagation speed Vus in the urea water, which is in the quiescent state. This increases the reliability of the determination concentration C1, and eventually increases the reliability of the determination result in the suitability of the urea water.

(2) The threshold $\Delta Tt$ has the greatest value among the thresholds of temperature difference with which it is determined that the urea water is in the quiescent state. This increases determining opportunity of the urea water in comparison to a case in which the smaller value among the thresholds is set to the threshold $\Delta Tt$.

(3) The maximum value $\Delta Tmax$ is the greatest value in the temperature difference between two temperatures selected from the urea water temperature Tu, the coolant temperature Tw, and the exhaust gas temperature Tex. The determination start condition includes that the maximum value $\Delta Tmax$ is less than or equal to the threshold $\Delta Tt$. These temperatures greatly change during operation of the engine 10. Such temperatures are selected as detection targets. Thus, when the determination start condition is satisfied, the reliability of the determination that the urea water is in the quiescent state is increased. As a result, the reliability of the determination concentration C1 is further increased.

(4) When the stopped condition is satisfied, the vehicle has been maintained in the stopped state from when the ignition was turned ON. In other words, the determination concentration C1 is calculated when the urea water is in the state without vibration caused by the moving vehicle. As a result, the reliability of the determination concentration C1 is increased.

(5) The stopped condition includes that the vehicle speed V is less than or equal to 0 km/h, that the brake information Binf is OFF, and that the gear information Ginf is N. Thus, when the stopped condition is satisfied, it is determined with certainty that the vehicle is in the stopped state.

(6) The improved reliability of the determination concentration C1 allows the normal range to be set narrower.

(7) The determination based on the newly acquired determination concentration C1 at step S13 is repeated until the stopped condition is no longer satisfied, i.e., until the vehicle starts moving. Thus, when starting the engine 10 changes the urea water temperature Tu, determination of suitability in the urea water is performed in multiple states. This increases reliability associated with the suitability of the urea water.

Second Embodiment

A urea water suitability determination device according to a second embodiment will now be described with reference to FIGS. 3 to 5. In the second embodiment, parts different from the first embodiment will be described in detail, and parts with similar functions to those in the first embodiment will not be described in detail by assigning like reference characters.

Figure 3:
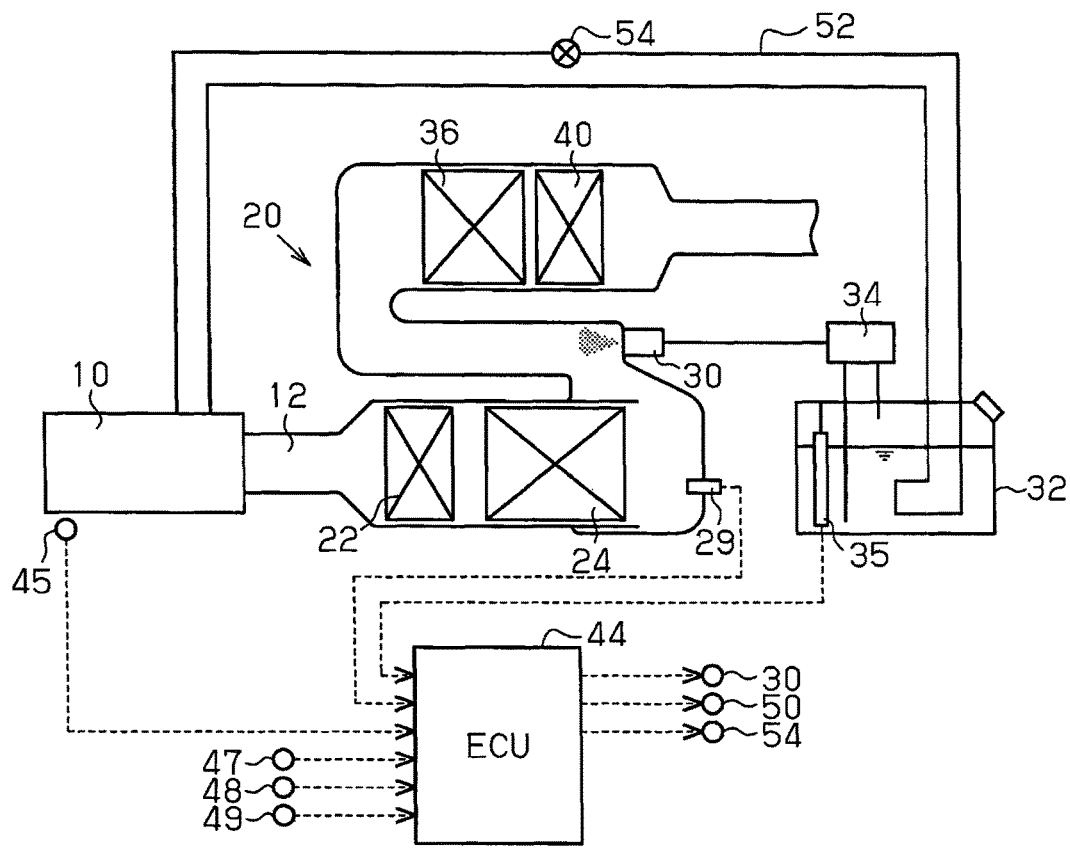
FIG. 3 is a schematic view of an exhaust gas purifier having a urea water suitability determination device according to a second embodiment.

As shown in FIG. 3, an exhaust gas purifier 20 according to the second embodiment includes a branch passage 52 divided from the coolant passage, through which the coolant passes to cool the engine 10. A portion of the branch passage 52 travels in the tank 32. A valve 54 is arranged in the branch passage 52, and opens or closes the branch passage 52. The opening and closing of the valve 54 is controlled by the ECU 44. When the valve 54 is in an open state, some of the coolant flows into the branch passage 52. Heat is exchanged between the coolant flowing through the branch passage 52 and the urea water in the tank 32. The branch passage 52 functions as a heating section for heating the urea water.

Figure 4:
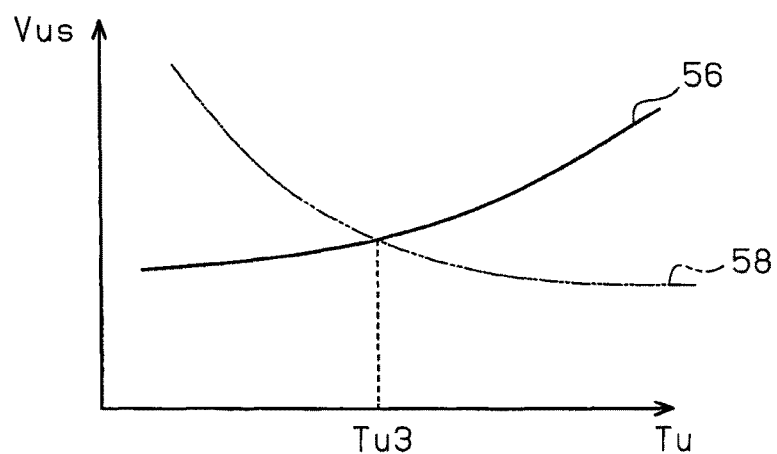
FIG. 4 is a graph showing one example of result in a comparison between a regular product and a counterfeit product in terms of the relationship between urea water temperature and propagation velocity of ultrasonic waves.

FIG. 4 is a graph illustrating the relationship between the urea water temperature Tu and the propagation speed Vus as an example of result when a regular product is compared to a counterfeit product. In FIG. 4, a solid line indicates a regular product 56, and a long dashed double-short dashed line indicates a counterfeit product 58. As shown in FIG. 4, the propagation speeds Vus in the regular product and the counterfeit product are the same at a urea water temperature Tu3. However, it is impossible that the propagation speeds Vus in the regular product and the counterfeit product are the same at every urea water temperature Tu. Thus, in the second embodiment, the suitability of the urea water is determined at two different urea water temperatures Tu.

According to the second embodiment, the ECU 44 executes a determination process, which will now be described with reference to FIG. 5. The determination process is executed every time the ignition of the vehicle is turned ON.

As shown in FIG. 5, the ECU 44 at the initial step S21 acquires various types of information, which includes an exhaust gas temperature Tex, a urea water temperature Tu1, a coolant temperature Tw, brake information Binf, gear information Ginf, and a vehicle speed V. At the next step S22, the ECU 44 determines whether the determination start condition is satisfied based on the various types of information.

When the determination start condition is not satisfied (step S22: NO), the ECU 44 finishes the determination process. In contrast, when the determination start condition is satisfied (step S22: YES), the ECU 44 acquires the determination concentration C1 from the sensor 35 (step S23).

At step S24, the ECU 44 determines whether the stopped condition is satisfied based on the various types of information acquired at step S21. When the stopped condition is not satisfied (step S24: NO), the ECU 44 finishes the determination process. In contrast, when the stopped condition is satisfied (step S24: YES), the ECU 44 determines whether the determination concentration C1, which is acquired at step S23, is within the normal range (step S25). The process at this step S25 is the first determining opportunity.

When the determination concentration C1 is within the normal range (step S25: YES), the ECU 44 opens the valve 54 at step S26 to cause some of the coolant to circulate through the branch passage 52. This heats the urea water in the tank 32 by exchanging heat with the coolant. Such heat exchange between the coolant and the urea water promotes an increase in the temperature of the urea water.

At step S27, the ECU 44 acquires a new urea water temperature Tu2 from the sensor 35. The ECU 44 calculates a changing amount $\Delta Tu$ ($\Delta Tu=Tu2-Tu1$) from the urea water temperature Tu1 acquired at step S21. The ECU 44 determines whether the changing amount £Tu exceeds a preset amount $\Delta Tut$ (step S28). As described above, the propagation speed Vus in the regular product becomes equal to the propagation speed Vus in the counterfeit product at the urea water temperature Tu3. Since the determination concentrations C1 are calculated based on the propagation speeds Vus, the determination concentrations C1 in the regular product also becomes equal to the determination concentrations C1 in the counterfeit product. The preset amount £Tut has a value, e.g., 10° C., that allows determination of whether the urea water is a regular product by using the determination concentration C2 based on the propagation speed Vus at the urea water temperature Tu2 even if the urea water temperature Tu1 is the urea water temperature Tu3. In this case, even if the urea water in the tank 32 is a counterfeit product, it is determined that the determination concentration C2 at the urea water temperature Tu2 certainly deviates from the normal range, which leads to the determination that the urea water is a regular product. The preset amount $\Delta Tut$ has a value provided in advance in the various types of data and is determined based on various experiments and simulations, which are performed in advance. The ECU 44 repeats the processes from step S27 to step S28 until the changing amount $\Delta Tu$ exceeds the preset amount $\Delta Tut$.

When the changing amount $\Delta Tu$ exceeds the preset amount $\Delta Tut$ (step S28: YES), the ECU 44 acquires a new determination concentration C2 from the sensor 35 (step S29) and determines whether the determination concentration C2 is within the normal range (step S30). The process at this step S30 is a second determining opportunity.

When the determination concentration C2 is within the normal range (step S30: YES), the ECU 44 determines that the urea water in the tank 32 is normal. The ECU 44 closes the valve 54 (step S31) and finishes a series of processes. In contrast, when the determination concentration C1 or C2 deviates from the normal range at step S25 or step S30, i.e., at the first and second determination opportunities, the ECU 44 activates the alarm 50 (step S32) and closes the valve 54 (step S31). The ECU 44 then finishes the series of processes.

Operation of the determination process which the ECU 44 executes in the second embodiment will now be described. In the determination process of the second embodiment, the determination concentrations C1 and C2 are calculated at two urea water temperatures Tut and Tu2, which differ at least by the preset amount $\Delta Tut$. Using the determination concentrations C1 and C2, the suitability of the urea water is determined. When any one of the determination concentrations C1 and C2 deviates from the normal range, it is determined that the urea water in the tank 32 is abnormal. In other words, the suitability of the urea water is determined at two different temperatures. This further increases the reliability of determination results in the suitability of the urea water.

The urea water suitability determination device according to the second embodiment achieves the following advantages in addition to the advantages (1) to (6), which are described in the first embodiment.

(8) The suitability of the urea water is determined at the first and second determination opportunities. This further increases the reliability of determination result in the suitability of the urea water.

(9) The heated urea water in the tank 32 accelerates the temperature increase of the urea water. This shortens the required time between the first determining opportunity and the second determining opportunity.

(10) Before many vibrations are given to the vehicle, i.e., when the urea water is in the quiescent state, the second determining opportunity is more easily obtained. This increases the reliability in the determination result at the second determining opportunity.

The above-illustrated embodiments may be modified in the following forms.

The determination process of the second embodiment may be modified as long as multiple determination opportunities are obtained at different urea water temperatures Tu. For example, both of the urea water temperatures Tu1 and Tu2 may be set in advance. A third determining opportunity may be set according to the changing amount of the urea water temperature Tu2. The start timing of the determination process is not limited to when the ignition is turned ON. For example, the determination process may be started after operation of the ignition or when the ignition is turned OFF. Even in the case in which the determination process is started when the ignition is turned OFF, multiple determination opportunities are obtained at different urea water temperatures, while the urea water temperature converges to the ambient temperature.

In the determination process of the second embodiment, the second determining opportunity is set based on the change amount ΔTu. Instead of this, the second determining opportunity may be set, for example, based on an amount of elapsed time from the first determining opportunity. The elapsed time may be changed according to a change in an operating state of the engine 10 after the first determining opportunity.

In the second embodiment, the heating section for heating the urea water is not limited to the branch passage 52, which is divided from the cooling passage of the engine. For example, the heating section may be an electronic device such as a heater or a passage divided from the exhaust passage 12, through which some of the exhaust gas flows.

In the determination process of the first and second embodiments, the stopped condition does not necessarily need to include three conditions, which are conditions in which V is less than or equal to 0 km/h, Binf=OFF, and Ginf=N. As long as the stopped condition includes a condition that allows determining that the vehicle is stopped, the first embodiment and the second embodiment may be modified. For example, the stopped condition may include only a condition associated with the vehicle speed V among the above three conditions. A new condition other than the three conditions may be added to the stopped condition.

In the determination process of the above-illustrated first and second embodiments, the stopped condition may be omitted. In other words, if the determination start condition is satisfied when the ignition is turned ON, the suitability of the urea water may be determined.

In the determination process of the first and second embodiments, an alternative condition may be set such that it is determined that the state of the urea water is maintained in the quiescent state. For example, the threshold Vt of the vehicle speed V may be replaced with 5 km/h.

In the determination process of the first embodiment, under a condition that the determination start condition and the stopped condition both are satisfied, the suitability of the urea water may be repeatedly determined. In other words, the ECU 44 may move to the process at step S12 when the process at step S18 in FIG. 2 is finished.

In the determination process of the above-illustrated first and second embodiments, detection targets of the temperature detecting section are not limited to the above three detection targets, i.e., the urea water, the coolant of the engine 10, and the exhaust passage of the engine 10. The detection targets of the temperature detecting section may include any targets having different temperatures on operation of the engine 10 in a space defined by the vehicle. For example, the detection targets may be any two of the three detection targets. The detection targets may include the ambient temperature, engine oil, and the like. Preferably, the highest temperatures of the detection targets that may be detected during operation of the engine 10 greatly differ. In addition, the exhaust passage as the detection targets is not limited to a portion of the exhaust passage 12. The exhaust passage may be a pipe itself, which forms the exhaust passage 12. In other words, the temperature detecting section may detect the temperature in the pipe of the exhaust passage 12 instead of the temperature in the exhaust passage 12.

In the above-illustrated first and second embodiments, the sensor 35 as the concentration detecting section outputs a urea water temperature Tu and a propagation speed Vus to the ECU 44. The ECU 44 may calculate the urea water concentration C based on the urea water temperature Tu and the propagation speed Vus. Furthermore, the ECU 44 is provided with data that defines a normal range of propagation speeds Vus at each urea water temperature Tu, and the suitability of the urea water may be determined based on the data.

In the above-illustrated first and second embodiments, the threshold may be set for each combination of any two selected detection targets. The threshold ΔTt may be set at the smallest value among the thresholds, which are set for each combination.

In the above illustrated first and second embodiments, the determination concentration C1 may be a concentration in the process at step S11, i.e., immediately before the determination start condition is satisfied.

The engine is not limited to a diesel engine. The engine may be a gasoline engine or natural gas engine.

The invention claimed is:

1. A urea water suitability determination device comprising:
a concentration detecting section, which detects a concentration of urea water and outputs the detected value;
a determining section, which determines whether the urea water is suitable by using the detected value output from the concentration detecting section; and
a temperature detecting section, which detects temperatures of a plurality of detection targets at different locations in a vehicle, wherein
the detection targets have temperatures that are different from one another during operation of an engine,
the determining section is adapted to:
calculate a temperature difference between a temperature of a particular detection target and a temperature of another detection target among the detection targets; and
when a determination start condition is satisfied, start determining whether the urea water is suitable,
the determination start condition includes that the temperature difference is within a reference range, and the reference range is defined as a range of temperature differences in which it is determined that the urea water is in a quiescent state, which is suitable for the determination, the detection targets include the urea water, the concentration detecting section is adapted to detect a concentration of the urea water based on a temperature of the urea water and a propagation velocity of an ultrasonic wave in the urea water, the determining section is adapted to:
  determine suitability of the urea water at a first determining opportunity, where the urea water is at a first temperature, and
determine suitability of the urea water at a second determining opportunity, where the urea water is at a second temperature, which is different from the first temperature, the urea water suitability determination device further comprises a heating section for heating the urea water, the determining section is adapted to:
  when the urea water is determined as suitable at the first determining opportunity, heat the urea water by the heating section,
  determine whether a changing amount of the urea water temperature from the first temperature exceeds a preset amount, and
  when the changing amount exceeds the preset amount, determines suitability of the urea water at the second determining opportunity.

2. The urea water suitability determination device according to claim 1, wherein each of the detection targets is used as the particular detection target.

3. The urea water suitability determination device according to claim 1, wherein:
  the detection targets are three or more detection targets, and
  an upper limit of the reference range is the largest value among temperature differences between the detection targets when it is determined that the urea water is in a quiescent state, which is suitable for the determination.

4. The urea water suitability determination device according to claim 1, wherein the detection targets include the urea water, coolant for cooling the engine, and an exhaust passage of the engine.

5. The urea water suitability determination device according to claim 1, wherein the determination start condition includes that the vehicle is in a stopped state.

* * * * *